US009908830B2

(12) United States Patent
Lee et al.

(10) Patent No.: US 9,908,830 B2
(45) Date of Patent: Mar. 6, 2018

(54) PREPARING METHOD OF A PHENOLIC OLIGOMER ANTIOXIDANT

(71) Applicant: KUMHO PETROCHEMICAL CO., LTD., Seoul (KR)

(72) Inventors: Hyung Jae Lee, Daejon (KR); Chang Kyo Shin, Daejon (KR); Seok Hyun Kang, Seoul (KR); Kyoung Ho Row, Daejon (KR); Ji Hyun Heo, Seoul (KR)

(73) Assignee: KUMHO PETROCHEMICAL CO., LTD, Seoul (KR)

( * ) Notice: Subject to any disclaimer, the term of this patent is extended or adjusted under 35 U.S.C. 154(b) by 0 days.

(21) Appl. No.: 15/228,373

(22) Filed: Aug. 4, 2016

(65) Prior Publication Data
US 2017/0174597 A1    Jun. 22, 2017

(30) Foreign Application Priority Data
Dec. 18, 2015 (KR) .................. 10-2015-0181565

(51) Int. Cl.
*C07C 37/14* (2006.01)
*C07C 37/70* (2006.01)
*C09K 15/08* (2006.01)
*C08G 61/02* (2006.01)

(52) U.S. Cl.
CPC .............. *C07C 37/14* (2013.01); *C07C 37/70* (2013.01); *C08G 61/02* (2013.01); *C07C 2103/68* (2013.01); *C07C 2603/68* (2017.05); *C08G 2261/1422* (2013.01); *C08G 2261/226* (2013.01); *C08G 2261/312* (2013.01); *C08G 2261/3325* (2013.01); *C08G 2261/45* (2013.01); *C08G 2261/596* (2013.01)

(58) Field of Classification Search
CPC ...... C07C 37/14; C07C 37/70; C07C 2103/68
See application file for complete search history.

(56) References Cited

U.S. PATENT DOCUMENTS 3,305,522 A     2/1967  Spacht
3,336,398 A  *  8/1967  Booth ................... C08F 232/08
                                                524/326

FOREIGN PATENT DOCUMENTS

| CN | 101402721 A | * | 4/2009 | ............ C08G 61/02 |
| CN | 101402721 A |   | 4/2009 | |
| CN | 101899142 A |   | 12/2010 | |
| CN | 101967223 A | * | 2/2011 | ............ C08G 61/02 |
| CN | 202219156 U | * | 5/2012 | ................ B01J 4/00 |

* cited by examiner

*Primary Examiner* — Rosalynd A Keys
(74) *Attorney, Agent, or Firm* — Whitham, Curtis & Cook, P.C.

(57) ABSTRACT

A method for preparing a phenolic oligomer antioxidant with a very small residual content of butylated hydroxytoluene (BHT) is provided.

Specifically, the method for preparing the phenolic oligomer antioxidant relates to a method which is capable of a BHT-free phenolic oligomer antioxidant or a phenolic oligomer antioxidant containing a trace amount of residual BHT by removing the precursor of BHT as much as possible by performing the concentration under the reduced pressure while injecting an inert gas to an intermediate product and/or removing BHT by performing the concentration under the reduced pressure while injecting an inert gas to the final product.

10 Claims, No Drawings

PREPARING METHOD OF A PHENOLIC OLIGOMER ANTIOXIDANT

CROSS-REFERENCE TO RELATED APPLICATIONS

This application claims, under 35 U.S.C. § 119, the priority of Korean Patent Application No. 10-2015-0181565, filed on Dec. 18, 2015, in the Korean Intellectual Property Office, the disclosure of which is incorporated herein by reference in its entirety.

BACKGROUND (a) Technical Field

The present invention relates to a method for preparing a phenolic oligomer antioxidant with a very small residual content of butylated hydroxytoluene (BHT).

(b) Background Art

In general, antioxidants added to polymers include phenolic antioxidants, amine-based antioxidants, phosphite-based antioxidant, thioester-based antioxidants, etc.

Although the phenolic antioxidants have superior thermal stability at the initial step of the oxidation process, their application is limited because they are discolored after the oxidation.

The amine-based antioxidants are also limited in their application because the materials have color themselves. The phosphite-based antioxidants are susceptible to hydrolysis, and easy to decompose during the vulcanization of the rubber. The thioester-based antioxidants are disadvantageous in that they do not show their distinct effect when used alone or together with other antioxidants.

Therefore, phenolic oligomer antioxidants are drawing attentions recently.

The phenolic oligomer antioxidant refers to an antioxidant wherein one or more monomer of diene compounds such as dicyclopentadiene (hereinafter, 'DCPD') is connected to the phenolic antioxidant.

The phenolic oligomer antioxidant is advantageous in that it prevents from the oxidation of polymers without negatively affecting the physical properties of the polymer. Also, because it is unharmful to the human body and has moderate volatility, it is widely used as a primary antioxidant that can be added to plastics, elastomers, mineral oils and synthetic oils.

Chinese Patent Publication No. 101402721 and U.S. Pat. No. 3,305,522 disclose, as a method for preparing the phenolic oligomer antioxidant, a method of adding an olefin to a phenolic oligomer compound, which is prepared from the reaction of a phenolic compound with DCPD thereto. However, the method according to the patent documents is problematic in that butylated hydroxytoluene (hereinafter, 'BHT') such as 2,6-di-tert-butyl-4-methylphenol is generated in large quantities during the preparation of the phenolic oligomer antioxidant.

Although the BHT is also used as a phenolic antioxidant, a variety of problems are reported. It can pollute the environment because it is highly volatile due to small molecular weight and the severe discoloration occurs upon its oxidation. What is worse, it is very harmful to the human body. It may be toxic to the liver and may cause allergy and tumors.

For this reason, demands on a BHT-free antioxidant are increasing rapidly.

REFERENCES OF THE RELATED ART

Patent Documents (Patent document 1) Chinese Patent Publication No. 101402721.
(Patent document 2) U.S. Pat. No. 3,305,522.

SUMMARY

The present invention has been made to overcome the above-described problems and limitations.

The present invention is directed to providing a method for preparing a phenolic oligomer antioxidant having the superior quality with a small residual content of BHT.

The purpose of the present invention is not limited to that stated above. The purpose of the present invention will become more evident by the following description and can be embodied by the means described in the claims and their combinations.

In an aspect, the present invention provides a method for preparing a phenolic oligomer antioxidant, which includes: (a) a step of reacting p-cresol with dicyclopentadiene (DCPD) in the presence of a boron fluoride catalyst; (b) a step of removing residual p-cresol by concentrating the product of the step (a) under the reduced pressure; (c) a step of reacting the product of the step (b) with isobutene in the presence of an acid; and (d) a step of obtaining a phenolic oligomer antioxidant with a residual content of butylated hydroxytoluene (BHT) of 500 ppm or less by concentrating the product of the step (c) under the reduced pressure while injecting an inert gas.

In the method for preparing a phenolic oligomer antioxidant according to the present invention, in the step (d), the inert gas may be injected through a gas line having a sparger- or tube-type tip.

In the method for preparing a phenolic oligomer antioxidant according to the present invention, the acid in the step (c) may be one or more selected from sulfuric acid, p-toluenesulfonic acid and methanesulfonic acid In the method for preparing a phenolic oligomer antioxidant according to the present invention, in the step (d), the concentration may be performed at a temperature of 170-250° C.

In the method for preparing a phenolic oligomer antioxidant according to the present invention, in the step (d), the concentration may be performed at a pressure of 20-100 mmHg.

In the method for preparing a phenolic oligomer antioxidant according to the present invention, in the step (d), the concentration may be performed at a gas hourly space velocity (GHSV) of the inert gas of 0.6-30 L/hr per 1 kg of the phenolic oligomer antioxidant.

In the method for preparing a phenolic oligomer antioxidant according to the present invention, in the step (b), p-cresol may be removed such that the residual content of p-cresol is 500 ppm or lower by concentrating under the reduced pressure while injecting an inert gas to the product of the step (a).

In the method for preparing a phenolic oligomer antioxidant according to the present invention, in the step (b), the inert gas may be injected through a gas line having a sparger- or tube-type tip.

In the method for preparing a phenolic oligomer antioxidant according to the present invention, in the step (b), the concentration may be performed at a temperature of 170-250° C.

In the method for preparing a phenolic oligomer antioxidant according to the present invention, in the step (b), the concentration may be performed at a pressure of 20-100 mmHg.

In the method for preparing a phenolic oligomer antioxidant according to the present invention, in the step (b), the concentration may be performed at a gas hourly space velocity (GHSV) of the inert gas of 0.6-30 L/hr per 1 kg of the product of step (a).

The present invention provides the following advantageous effects.

In the method for preparing a phenolic oligomer antioxidant according to the present invention, BHT generated during the preparation can be removed effectively, and thus products having the remarkable marketability may be produced.

Also, in accordance with the method for preparing a phenolic oligomer antioxidant according to the present invention, a BHT-free antioxidant or an antioxidant containing residual BHT in a trace amount can be prepared.

Also, in accordance with the method for preparing a phenolic oligomer antioxidant according to the present invention, a BHT-free phenolic oligomer antioxidant which is environmentally friendly and unharmful to the human body can be provided.

Also, in accordance with the method for preparing a phenolic oligomer antioxidant according to the present invention, a high-quality product can be produced without a cost increase because BHT can be removed effectively without an expensive concentrating facility. Accordingly, a phenolic oligomer antioxidant with high quality competitiveness and cost competitiveness can be produced.

The effects of the present invention are not limited to those described above. It is to be understood that all effects that can be inferred from the following description are included in the effects of the present invention.

DETAILED DESCRIPTION

Hereinafter, the present invention is described in detail through exemplary embodiments. The exemplary embodiments of the present invention can be modified in the various forms within the range not changing the subject matter of the present invention and the scope of the present invention is not limited by the exemplary embodiments.

In the following description, the description of known features and functions will be omitted in order to avoid obscuring the subject matter of the present invention.

In the following description, "include" means that additional constituents can be further included unless specified otherwise.

When preparing a phenolic oligomer antioxidant by the existing method, butylated hydroxytoluene (BHT) such as 2,6-di-tert-butyl-4-methylphenol is generated for the following reasons.

The phenolic oligomer antioxidant may be prepared by reacting a phenolic compound with dicyclopentadiene (DCPD), followed by reacting an olefin with the intermediate product. The phenolic compound is added in excess so that the DCPD is reacted completely. As a result, a large amount of the phenolic compound remains in the intermediate product, and then the phenolic compound, which remained even after the evaporation under the reduced pressure, reacts with the olefin to produce dialkylated phenolic compound.

For example, when p-cresol is used as the phenolic compound and isobutene is used as the olefin, residual p-cresol remaining in the intermediate product reacts with isobutene to generate 2,6-di-tert-butyl-4-methylphenol (BHT) as follows.

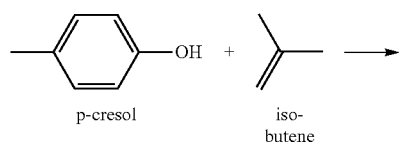

p-cresol   iso-
           butene

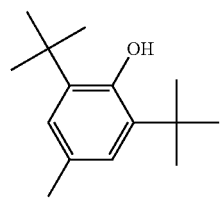

2,6-di-tert-butyl-4-
methylphenol

As described above, the BHT can pollute the environment because it is highly volatile and also its severe discoloration occurs upon the oxidation. In the existing art, the BHT can be removed by evaporating the final product. However, there is a limitation in removing the BHT simply through the concentration under the reduced pressure because the phenolic oligomer antioxidant is highly viscous.

Therefore, the inventors of the present invention provide a method for preparing a phenolic oligomer antioxidant, which is capable of removing BHT more effectively.

The method for preparing a phenolic oligomer antioxidant according to the present invention may include: (a) a step of reacting p-cresol with dicyclopentadiene (DCPD) in the presence of a boron fluoride catalyst; (b) a step of removing residual p-cresol by concentrating the product of the step (a) under the reduced pressure; (c) a step of reacting the product of the step (b) with isobutene in the presence of an acid; and (d) a step of obtaining a phenolic oligomer antioxidant with a residual content of butylated hydroxytoluene (BHT) of 500 ppm or less by concentrating the product of the step (c) under the reduced pressure while injecting an inert gas.

In the step (a), p-cresol may be added in excess to completely react DCPD. Accordingly, the intermediate product obtained in the step (a) may contain i) phenolic oligomeric products of p-cresol and DCPD and ii) p-cresol remaining after the reaction is completed.

In the step (b), the residual p-cresol is removed by concentrating the intermediate product under reduced pressure. As described above, because the phenolic compound such as p-cresol can become a precursor to BHT, it may be preferable to decrease its residual content as much as possible before adding isobutene.

However, because phenolic oligomeric products of the intermediate product have a very high viscosity, it is difficult to remove p-cresol from the intermediate product through the simple concentration.

Accordingly, in the present invention, the concentration under the reduced pressure in the step (b) is performed under the following condition such that the residual content of p-cresol in the intermediate product is 500 ppm or lower.

In the step (b), the intermediate product may be concentrated under the reduced pressure at a temperature of 150-280° C., specifically 170-250° C. When the temperature is lower, concentration may be difficult due to the increased viscosity of the intermediate product and its discoloration may occur at the higher temperatures.

And, in the step (b), the intermediate product may be concentrated under the reduced pressure at a pressure (degree of vacuum) of 200 mmHg or lower, specifically 100 mmHg or lower, more specifically 20-100 mmHg. When the pressure is higher, it may be difficult to remove p-cresol due to the decreased effect of the concentration under the reduced pressure. Also, its discoloration may occur due to the increased concentration time.

In the step (b), the concentration under the reduced pressure may be performed while injecting an inert gas to the intermediate product. The inert gas which does not react with the intermediate product is injected to ensure purging of p-cresol.

As described above, the intermediate product contains phenolic oligomeric products of p-cresol and DCPD and residual p-cresol. Because p-cresol has a smaller molecular weight than phenolic oligomeric products of p-cresol and DCPD, it has relatively lower viscosity. Therefore, p-cresol having the low viscosity can be separated from the intermediate product by injecting an inert gas which does not react with the intermediate product.

The inert gas is not limited as long as it is a gas which does not react with the intermediate product. Specifically, nitrogen gas may be used.

In the step (b), the inert gas may be injected at a gas hourly space velocity (GHSV) of 0.1-100 L/hr, specifically 0.6-30 L/hr, per 1 kg of the intermediate product. When the space velocity is lower, the effect of separating p-cresol may be insignificant. And, when the space velocity is higher, it may be economically disadvantageous because phenolic oligomeric products of p-cresol and DCPD may be removed together.

In the present invention, the 'space velocity' refers to the flow rate of a feed gas with respect to the mass of a substance to which the gas is injected. It can be measured by adjusting the mass of the substance and the flow rate of the gas.

In the step (b), the inert gas may be injected through a gas line. The gas line may have a sparger- or tube-type tip.

When the gas line has a sparger-type tip, the inert gas may be injected through spraying. Specifically, the sparger-type tip may be formed of a porous sintered metal membrane.

To summarize, in accordance with the present invention, the temperature and pressure are controlled during the concentration under the reduced pressure in the step (b) so as to decrease the viscosity of the intermediate product and then p-cresol with the decreased viscosity is purged by injecting an inert gas under a specific condition to remove p-cresol from the intermediate product.

In the step (c), the phenolic oligomer antioxidant is prepared by adding isobutene to the intermediate product obtained in the step (b) in the presence of an acid catalyst.

The acid catalyst may be one or more acid catalyst selected from sulfuric acid, p-toluenesulfonic acid and methanesulfonic acid.

In the step (c), BHT may not be generated if isobutene is added after the residual p-cresol has been completely removed in the step (b). But, if a trace amount of the residual p-cresol remains, BHT may be generated through the reaction of the residual p-cresol with isobutene.

Accordingly, the product obtained in the step (c) may contain i) a phenolic oligomer antioxidant such as butylated phenolic oligomeric products obtained from butylation of phenolic oligomeric products and ii) BHT obtained from butylation of p-cresol.

In the step (d), BHT is removed by concentrating the product under the reduced pressure. The product is highly viscous at the temperature of the concentration because the phenolic oligomer antioxidant has a large molecular weight. Therefore, it is difficult to remove BHT from the product through the simple concentration.

Accordingly, in accordance with the present invention, a phenolic oligomer antioxidant with a residual content of BHT of 500 ppm or less is obtained by performing the concentration under the reduced pressure in the step (d) under the following conditions.

In the step (d), the product of the step (c) may be concentrated under the reduced pressure by controlling the temperature to 150-280° C., specifically 170-250° C. When the temperature is lower, it may be difficult to concentrate because the viscosity of the product is increased. In addition, its discoloration may occur at the higher temperatures.

And, in the step (d), the product of the step (c) may be concentrated under the reduced pressure at a pressure (degree of vacuum) of 200 mmHg or lower, specifically 100 mmHg or lower, more specifically 20-100 mmHg. When the pressure is higher, it may be difficult to remove BHT due to the decreased effect of the concentration under the reduced pressure. Also, its discoloration may occur due to the increased concentration time.

In the step (d), the product of the step (c) may be concentrated under the reduced pressure while injecting an inert gas. The inert gas which does not react with the phenolic oligomer antioxidant is injected to ensure purging of BHT.

As described above, the product of the step (c) contains the phenolic oligomer antioxidant and BHT. BHT has a smaller molecular weight than the phenolic oligomer antioxidant. Accordingly, it has a relatively lower viscosity and, therefore, only BHT can be separated from the phenolic oligomer antioxidant by injecting an inert gas under the reduced pressure.

The inert gas is not limited as long as it is a gas which does not react with the phenolic oligomer antioxidant. Specifically, nitrogen gas may be used.

In the step (d), the inert gas may be injected at a gas hourly space velocity (GHSV) of 0.1-100 L/hr, specifically 0.6-30 L/hr, per 1 kg of the product of the step (c). When the space velocity is lower, the effect of separating BHT may be insignificant. And, when the space velocity is higher, it may be economically disadvantageous because the phenolic oligomer antioxidant may be removed together.

In the step (d), the inert gas may be injected through a gas line. The gas line may have a sparger- or tube-type tip.

When the gas line has a sparger-type tip, the inert gas may be injected through spraying. Specifically, the sparger-type tip may be formed of a porous sintered metal membrane.

To summarize, in accordance with the present invention, the temperature and pressure are controlled during the concentration under the reduced pressure in the step (d) so as to decrease the viscosity of the product of the step (c) and then BHT is purged by injecting an inert gas under a specific condition to remove it.

The method for preparing a phenolic oligomer antioxidant according to the present invention is described in more detail through examples.

The following examples have illustrative purposes only and the scope of this invention is not limited by them.

(1) Preparation of Intermediate Product and Removal of P-Cresol

After adding p-cresol (130 g) to boron trifluoride etherate (3.0 g), the solution was heated to 80° C. Then, dicyclopentadiene (90 g) was slowly added at 100° C. for 3 hours. Subsequently, an intermediate product was prepared by further reacting for 2 hours.

In Example 1~7, p-cresol was removed by primarily concentrating the intermediate product with the injection of nitrogen under the pressure and the temperature conditions shown in Table 1.

In Comparative Example 1, p-cresol was removed by performing the concentration under the reduced pressure without the injection of nitrogen (inert gas).

TABLE 1

| | Concentration temperature [° C.] | Concentration pressure [mmHg] | Nitrogen inlet type | Nitrogen gas injection time [min] | Nitrogen gas space velocity [L/hr] | p-Cresol residual content [ppm] |
|---|---|---|---|---|---|---|
| Example 1 | 190 | 20 | tube | 90 | 0.6 | 310 |
| Example 2 | 190 | 20 | tube | 90 | 1.2 | 80 |
| Example 3 | 190 | 20 | tube | 50 | 6 | 0 |
| Example 4 | 190 | 50 | tube | 90 | 6 | 140 |
| Example 5 | 190 | 100 | tube | 90 | 6 | 340 |
| Example 6 | 190 | 20 | sparger | 90 | 0.6 | 40 |
| Example 7 | 190 | 20 | sparger | 90 | 3 | 0 |
| Comparative Example 1 | 190 | 20 | — | — | — | 3,250 |

As seen from Table 1, when only the temperature and pressure were controlled without the injection of nitrogen (Comparative Example 1), the residual content of p-cresol was 3,250 ppm.

In contrast, the residual content of p-cresol was 500 ppm or less in Examples 1-7. In particular, p-cresol was completely removed and not detected in Example 3 and Example 7.

Therefore, when step (c) and step (d) are performed using the above Examples 1 to 7, the residual content of BHT in the final product can be 500 ppm or less. In particular, BHT will not be produced at all in Example 3 and Example 7.

(2) Preparation of Phenolic Oligomer Antioxidant and Removal of BHT

The intermediate product (120 g) obtained from Comparative Example 1 was cooled and then dissolved in 160 g of toluene as a solvent. After adding p-toluenesulfonic acid (7.5 g) as an acid catalyst, reaction was performed by injecting isobutene gas (60 g) at 80° C. for 1 hour.

After the reaction was completed, toluene (220 g) was added and the reaction mixture was neutralized with an aqueous sodium carbonate solution. Then, a final product was obtained by removing the aqueous layer.

In Example 8 to 14, a phenolic oligomer antioxidant was obtained by removing BHT from the final product by the secondary concentration with the injection of nitrogen under the pressure and the temperature conditions illustrated in Table 2.

In Comparative Example 2, BHT was removed by performing the concentration under the reduced pressure without the injection of nitrogen (inert gas).

As seen from Table 2, the residual content of BHT remaining in a phenolic oligomer antioxidant before the concentration was 5,700 ppm and the residual content of BHT when only the temperature and pressure were controlled without injection of nitrogen (Comparative Example 2) was 1,450 ppm.

In contrast, the residual content of BHT remaining in a phenolic oligomer antioxidant was 500 ppm or less in Examples 8-14. In particular, BHT was completely removed and not detected in Example 10 and Example 14.

As seen from Example 8 to 14, the residual content of BHT remaining in a phenolic oligomer antioxidant can be 500 ppm or less by concentrating the phenolic oligomer antioxidant under reduced pressure while injecting the inert gas in step (d).

The present invention has been described in detail with reference to exemplary embodiments thereof. However, it will be appreciated by those skilled in the art that the various changes and the modifications may be made in these embodiments without departing from the principles and spirit of the invention, the scope of which is defined in the appended claims and their equivalents.

What is claimed is:

1. A method for preparing a phenolic oligomer antioxidant, which comprises:
    (a) reacting p-cresol with dicyclopentadiene (DCPD) in the presence of a boron fluoride catalyst;
    (b) removing residual p-cresol to 500 ppm or less by concentrating a product of (a) under reduced pressure;
    (c) reacting a product of (b) with isobutene in the presence of an acid; and

TABLE 2

| | Concentration temperature [° C.] | Concentration pressure [mmHg] | Nitrogen inlet type | Nitrogen gas injection time [min] | Nitrogen gas space velocity [L/hr] | BHT residual content [ppm] |
|---|---|---|---|---|---|---|
| Example 8 | 200 | 20 | tube | 90 | 0.6 | 470 |
| Example 9 | 200 | 20 | tube | 90 | 1.2 | 110 |
| Example 10 | 200 | 20 | tube | 50 | 6 | 0 |
| Example 11 | 200 | 50 | tube | 90 | 6 | 210 |
| Example 12 | 200 | 100 | tube | 90 | 6 | 450 |
| Example 13 | 200 | 20 | sparger | 90 | 0.6 | 50 |
| Example 14 | 200 | 20 | sparger | 90 | 3 | 0 |
| Comparative Example 2 | 200 | 20 | — | — | — | 1,450 |
| Comparative Example 2 (Before concentration) | — | 760 | — | — | — | 5,700 |

(d) obtaining a phenolic oligomer antioxidant with a residual content of butylated hydroxytoluene (BHT) of 500 ppm or less by concentrating a product of (c) under the reduced pressure, wherein one or more of steps (b) and (d) are performed while injecting an inert gas through a gas line having one of a sparger type tip and tube type tip with a gas hourly space velocity (GHSV) of the inert gas for the concentration of the product of step (a) or (c) respectively is 0.6-30 L/hr per 1 kg of the product of step (a) or (c) respectively.

2. The method for preparing the phenolic oligomer antioxidant according to claim 1, wherein the acid in (c) is one or more selected from sulfuric acid, p-toluenesulfonic acid, and methanesulfonic acid.

3. The method for preparing the phenolic oligomer antioxidant according to claim 1, wherein, in (d), the temperature for the concentration of the product of step (c) is 170-250° C.

4. The method for preparing the phenolic oligomer antioxidant according to claim 1, wherein, in (d), the pressure for the concentration of the product of step (c) is 100 mmHg or lower.

5. The method for preparing the phenolic oligomer antioxidant according to claim 1, wherein in step (d) the GHSV of the inert gas for the concentration of the product of step (c) is 0.6-30 L/hr per 1 kg of the product of step (c).

6. The method for preparing the phenolic oligomer antioxidant according to claim 1, wherein, (b) is performed while injecting the inert gas to the product of (a).

7. The method for preparing a phenolic oligomer antioxidant according to claim 6, wherein, in (b), the temperature for the concentration of the product of step (a) is 170-250° C.

8. The method for preparing the phenolic oligomer antioxidant according to claim 6, wherein, in (b), the pressure for the concentration of the product of step (a) is 100 mmHg or lower.

9. The method for preparing a phenolic oligomer antioxidant according to claim 6, wherein in step (b) GHSV of the inert gas for the concentration of the product of step (a) is 0.6-30 L/hr per 1 kg of the product of step (a).

10. The method for preparing a phenolic oligomer antioxidant according to claim 1 wherein
in step (b) the GHSV of the inert gas for the concentration of the product of step (a) is 0.6-30 L/hr per 1 kg of the product of step (a), and
in step (d) the GHSV of the inert gas for the concentration of the product of step (c) is 0.6-30 L/hr per 1 kg of the product of step (c).

\* \* \* \* \*